US010028672B2

(12) United States Patent
Huang et al.

(10) Patent No.: US 10,028,672 B2
(45) Date of Patent: Jul. 24, 2018

(54) WEARABLE DEVICE WHICH DIAGNOSIS PERSONAL CARDIAC HEALTH CONDITION BY MONITORING AND ANALYZING HEARTBEAT AND THE METHOD THEREOF

(71) Applicants: ACME PORTABLE CORP., New Taipei (TW); ACME PORTABLE MACHINES, INC., Azusa, CA (US)

(72) Inventors: Ching Huang, Taipei (TW); Changyu Liu, Yuanlin (TW); Tsair Kao, New Taipei (TW)

(73) Assignees: ACME Portable Corp., New Taipei (TW); ACME Portable Machines, Inc., Azusa, CA (US)

( * ) Notice: Subject to any disclaimer, the term of this patent is extended or adjusted under 35 U.S.C. 154(b) by 0 days.

(21) Appl. No.: 15/015,967

(22) Filed: Feb. 4, 2016

(65) Prior Publication Data
US 2017/0135593 A1    May 18, 2017

(30) Foreign Application Priority Data

Nov. 13, 2015 (TW) .............................. 104137590 A

(51) Int. Cl.
*A61B 5/046* (2006.01)
*A61B 5/024* (2006.01)
(Continued)

(52) U.S. Cl.
CPC .......... *A61B 5/046* (2013.01); *A61B 5/02405* (2013.01); *A61B 5/02416* (2013.01);
(Continued)

(58) Field of Classification Search
CPC ............ A61B 5/02405; A61B 5/02416; A61B 5/02438; A61B 5/046; A61B 5/11;
(Continued)

(56) References Cited

U.S. PATENT DOCUMENTS 5,086,772 A * 2/1992 Larnard ............... A61N 1/3962
607/4
5,607,460 A * 3/1997 Kroll .................. A61N 1/37247
607/30
(Continued)

FOREIGN PATENT DOCUMENTS

EP         2443996 A1     4/2012

OTHER PUBLICATIONS

Extended European Search Report issued in European Application No. 16182885.0; dated Mar. 30, 2017 (11 pages).

*Primary Examiner* — Christopher A Flory
(74) *Attorney, Agent, or Firm* — Osha Liang LLP

(57) ABSTRACT

A wearable device which diagnoses personal cardiac health condition by monitoring and analyzing heartbeat includes a motion sensor detecting whether the user is in a motion state; a heart rhythm sensor detecting the user's signal of heartbeat interval; a memory storing algorithm program and database for data process, comparison, and analysis; a microprocessor calculating, filtering and judging the signal of heartbeat interval; and a feedback module displaying or alarming a judgment result, wherein the wearable device continuously detects the user's motion state and heartbeat condition, and detects heart rhythm when the user is not in the motion state to further judge the user's cardiac health condition, such as atrial fibrillation.

6 Claims, 6 Drawing Sheets

(51) Int. Cl.
*A61B 5/00* (2006.01)
*A61B 5/0468* (2006.01)
*A61B 5/11* (2006.01)

(52) U.S. Cl.
CPC ........ *A61B 5/02438* (2013.01); *A61B 5/0468* (2013.01); *A61B 5/11* (2013.01); *A61B 5/721* (2013.01); *A61B 5/7285* (2013.01); *A61B 5/742* (2013.01); *A61B 5/7405* (2013.01)

(58) Field of Classification Search
CPC ..... A61B 5/721; A61B 5/7285; A61B 5/7405; A61B 5/742
USPC ................................................ 600/509, 515
See application file for complete search history.

(56) References Cited

U.S. PATENT DOCUMENTS

| | | | | |
|---|---|---|---|---|
| 5,919,141 A * | 7/1999 | Money | A61B 5/02055 | 600/483 |
| 9,301,702 B2 * | 4/2016 | Ngo | A61B 5/0006 | |
| 9,642,529 B1 * | 5/2017 | Siddiqui | A61B 5/0008 | |
| 9,681,819 B2 * | 6/2017 | Wiesel | A61B 5/024 | |
| 9,724,007 B2 * | 8/2017 | Cole | A61B 5/0452 | |
| 2002/0065473 A1 | 5/2002 | Wang et al. | | |
| 2003/0120164 A1 * | 6/2003 | Nielsen | A61B 5/02055 | 600/513 |
| 2003/0144597 A1 | 7/2003 | Bock | | |
| 2005/0004486 A1 * | 1/2005 | Glass | A61B 5/02405 | 600/515 |
| 2006/0195037 A1 | 8/2006 | Wiesel | | |
| 2007/0167852 A1 * | 7/2007 | Sugo | A61B 5/029 | 600/513 |
| 2008/0097537 A1 * | 4/2008 | Duann | A61B 5/0452 | 607/14 |
| 2008/0108880 A1 * | 5/2008 | Young | A61B 5/0022 | 600/300 |
| 2008/0146889 A1 * | 6/2008 | Young | A61B 5/0205 | 600/300 |
| 2008/0167534 A1 * | 7/2008 | Young | G06F 19/3418 | 600/301 |
| 2009/0243833 A1 * | 10/2009 | Huang | G06F 19/323 | 340/505 |
| 2009/0322513 A1 * | 12/2009 | Hwang | A61B 5/02055 | 340/539.12 |
| 2010/0049070 A1 * | 2/2010 | Kao | A61B 5/02405 | 600/521 |
| 2010/0268518 A1 * | 10/2010 | Sugo | A61B 5/0285 | 703/2 |
| 2011/0160601 A1 * | 6/2011 | Wang | A61B 5/04085 | 600/509 |
| 2014/0031703 A1 * | 1/2014 | Rayner | A61B 5/02055 | 600/484 |
| 2014/0066732 A1 * | 3/2014 | Addison | A61B 5/029 | 600/324 |
| 2014/0078694 A1 * | 3/2014 | Wissmar | G04G 17/04 | 361/749 |
| 2014/0114167 A1 * | 4/2014 | Reaser, Jr. | A61B 5/046 | 600/393 |
| 2014/0135631 A1 * | 5/2014 | Brumback | A61B 5/02438 | 600/479 |
| 2014/0142403 A1 * | 5/2014 | Brumback | A61B 5/02433 | 600/324 |
| 2014/0176335 A1 * | 6/2014 | Brumback | A61B 5/0015 | 340/870.01 |
| 2014/0176346 A1 * | 6/2014 | Brumback | A61B 5/0015 | 340/870.16 |
| 2014/0176422 A1 * | 6/2014 | Brumback | A61B 5/0015 | 345/156 |
| 2014/0180136 A1 * | 6/2014 | Su | A61B 5/7221 | 600/479 |
| 2014/0180595 A1 * | 6/2014 | Brumback | A61B 5/0015 | 702/19 |
| 2014/0197946 A1 * | 7/2014 | Park | G08B 21/18 | 340/539.11 |
| 2014/0197963 A1 * | 7/2014 | Park | G08B 21/18 | 340/870.01 |
| 2014/0197965 A1 * | 7/2014 | Park | G08B 21/18 | 340/870.09 |
| 2014/0228649 A1 * | 8/2014 | Rayner | A61B 5/1118 | 600/301 |
| 2014/0278139 A1 * | 9/2014 | Hong | A61B 5/4866 | 702/19 |
| 2014/0303523 A1 * | 10/2014 | Hong | A61B 5/4866 | 600/595 |
| 2014/0378786 A1 * | 12/2014 | Hong | A61B 5/4866 | 600/301 |
| 2014/0378787 A1 * | 12/2014 | Brumback | A61B 5/02433 | 600/301 |
| 2014/0378872 A1 * | 12/2014 | Hong | A61B 5/4866 | 600/595 |
| 2015/0018693 A1 * | 1/2015 | Mestha | A61B 5/7282 | 600/479 |
| 2015/0042471 A1 * | 2/2015 | Park | G08B 21/18 | 340/539.12 |
| 2015/0065891 A1 | 3/2015 | Wiesel | | |
| 2015/0094831 A1 * | 4/2015 | Brumback | G06F 19/3406 | 700/91 |
| 2015/0094832 A1 * | 4/2015 | Brumback | G06F 19/3406 | 700/91 |
| 2015/0109124 A1 * | 4/2015 | He | G06F 21/00 | 340/539.12 |
| 2015/0112154 A1 * | 4/2015 | He | G06F 21/00 | 600/301 |
| 2015/0112155 A1 * | 4/2015 | Bijjani | G06F 21/00 | 600/301 |
| 2015/0112156 A1 * | 4/2015 | He | G06F 21/00 | 600/301 |
| 2015/0112157 A1 * | 4/2015 | Bijjani | G06F 21/00 | 600/301 |
| 2015/0112158 A1 * | 4/2015 | He | G06F 21/00 | 600/301 |
| 2015/0112159 A1 * | 4/2015 | He | G06F 21/00 | 600/301 |
| 2015/0112208 A1 * | 4/2015 | He | G06F 21/00 | 600/479 |
| 2015/0112452 A1 * | 4/2015 | He | G06F 21/00 | 700/11 |
| 2015/0230761 A1 * | 8/2015 | Brumback | A61B 5/7475 | 600/479 |
| 2015/0231446 A1 * | 8/2015 | Brumback | A63B 24/0062 | 700/91 |
| 2015/0245801 A1 * | 9/2015 | Brumback | G06F 19/3406 | 700/91 |
| 2015/0294554 A1 * | 10/2015 | Park | G08B 21/18 | 340/539.11 |
| 2016/0000349 A1 * | 1/2016 | Sullivan | A61B 5/04012 | 600/509 |
| 2016/0034634 A9 * | 2/2016 | Hong | A61B 5/4866 | 702/19 |
| 2016/0058391 A1 * | 3/2016 | Narusawa | A61B 5/681 | 600/301 |
| 2016/0120433 A1 * | 5/2016 | Hughes | G16H 40/63 | 600/483 |
| 2016/0120434 A1 * | 5/2016 | Park | G16H 40/63 | 600/301 |
| 2016/0267764 A1 * | 9/2016 | Park | G08B 21/18 | |
| 2016/0278659 A1 * | 9/2016 | Kaib | A61B 5/04525 | |
| 2016/0302677 A1 * | 10/2016 | He | A61B 5/02125 | |
| 2016/0361021 A1 * | 12/2016 | Salehizadeh | A61B 5/0245 | |
| 2017/0014037 A1 * | 1/2017 | Coppola | A61B 5/6898 | |
| 2017/0020399 A1 * | 1/2017 | Shemesh | A61B 5/0205 | |
| 2017/0079537 A1 * | 3/2017 | McEwen | A61B 5/0004 | |
| 2017/0135585 A1 * | 5/2017 | Liu | A61B 5/0059 | |
| 2017/0143239 A1 * | 5/2017 | Park | A61B 5/1118 | |
| 2017/0188872 A1 * | 7/2017 | Hughes | A61B 5/04087 | |
| 2017/0367602 A1 * | 12/2017 | Sullivan | A61N 1/3993 | |

* cited by examiner

WEARABLE DEVICE WHICH DIAGNOSIS PERSONAL CARDIAC HEALTH CONDITION BY MONITORING AND ANALYZING HEARTBEAT AND THE METHOD THEREOF

FIELD OF THE INVENTION

The present invention relates to a wearable device, particularly relates to a wearable device which diagnoses personal cardiac health condition by monitoring and analyzing heartbeat and the method thereof.

BACKGROUND OF THE INVENTION

In past, apparatus of detecting physiological function is often of huge volume so as to be put in a health center, and people can't help but go to the health center where it is put for detecting health condition. At that time, it is not easy for people to execute detection at any time they want. However, along with progress of medical and semiconductor technologies, present detection apparatus has been of smaller volume and further able to be mounted onto body, which is called wearable device with real time detection.

Present wearable device may detect user's various physiological data, such as body temperature, breathe, heartbeat, pedestrian time or distance, and so on. Among these physiological data, heartbeat may reflect important information about personal health. Heart rhythm represents signal of heartbeat interval in a fixed period and reflects heart condition. There are two detection approaches for heart rhythm: optical transmittance measurement and electric signal measurement. The optical transmittance measurement is also called photoplethysmography, which illuminates skin and measures changes in light absorption or reflection for acquisition of heartbeat condition. The principle of the optical transmittance measurement is based on constant light absorption by skin or muscle tissue at specific zones of human body, but amount of light absorption can be influenced by blood volume within skin. When heart pumps, the blood volume within skin can have pulsation change. When heart contracts, peripheral blood volume is the biggest, so that light absorption is the most, too. Accordingly, when there is a little change in reflected light detected by light sensor, it is supposed to have one heartbeat. Because there is specific wavelength light absorption for blood, huge amount of light of the specific wavelength will be absorbed when heart pumps every time, and heartbeat may be determined by measuring reflected or absorbed light signal. However, too much power consumption and its subjected to interference by ambient light outside are disadvantages for optical transmittance measurement. On the other hands, electric signal measurement has a principle similar to electrocardiogram method, which direct measures electric signals generated from heart beats by a sensor to judge user's heart rhythm condition. There are drawbacks for such a method, such as complicated circuit and the sensor needed to be tightly attached onto skin and fixed, so it is not suitable for wearable device like wrist ring or watch.

Present wearable devices often utilize optical transmittance measurement to monitor user's heart beats because of its light weight and compact volume to reduce user's loading when wearing it. Thus, how to analyze the signal detected by optical transmittance measurement for wearable device will influence analysis accuracy for physiological signal and become a key issue. On the other hand, complicated analysis method not only utilizes huge circuit for processing but also causes much power consumption to reduce power continue voyage ability in standby. Thus, how to make balances among detection accuracy, low consumption, and light and compact volume is an important issue for designing wearable device.

In order to resolve the drawbacks aforementioned, there are technologies to look for wearable device cooperated with portable device. With wireless transmission, the wearable device transmits detected signal to portable device for performing analysis and display of the detected signal. Though circuit volume and power consumption of wearable device may not be influenced even with more complex analysis and calculation, however, such cooperation approach results in wearable device unable to use independently, and user needs to pick up portable device for checking physiological condition. Both convenience and intuitiveness in use will be destroyed. Thus, it is not a perfect solution. Besides, over power consumption is still an issue because wearable device still transmits huge volume signals to exterior device by wireless transmission method.

Accordingly, subject to low power consumption and rapid calculation, it is an important issue of the present invention to have a design capable of rapidly detecting signal and analyzing detected signal to provide user precise and accurate physiological data such as heat beat or rhythm.

SUMMARY OF THE INVENTION

For there is not wearable device to accurately detect user's heartbeat and rhythm physiological signal under low power consumption, so a method of diagnosing personal cardiac health condition by monitoring and analyzing heartbeat is provided herein to reduce unnecessary signal process and power consumption by detecting a motion state in advance. Furthermore, the detected signals are filtered and judged many times to enhance accuracy of data judgment.

Accordingly, a method of diagnosing personal cardiac health condition by monitoring and analyzing heartbeat includes following steps: (1) judging whether a user is in a motion state; (2) detecting the user's heartbeat signal when the user is judged not to be in the motion state; (3) judging whether there is atrial fibrillation by calculating the heartbeat signal to acquire a signal of heartbeat interval; and (4) judging whether there is arrhythmia by using abnormal heartbeat detection for the user's heartbeat signal.

Accordingly, a wearable device performing the method aforementioned includes: a motion sensor detecting whether the user is in a motion state; a heart rhythm sensor detecting the user's signal of heartbeat interval; a memory storing algorithm program and database for data process, comparison, and analysis; a microprocessor calculating, filtering and judging the signal of heartbeat interval; and a feedback module displaying or alarming a judgment result, wherein the wearable device continuously detects the user's motion state and heartbeat condition, and detects heart rhythm when the user is not in the motion state to further judge the user's cardiac health condition.

Accordingly, the precise degree of estimating health signal may be enhanced with multiple thorough calculation and filtration for signals in the method of diagnosing personal cardiac health condition by monitoring and analyzing heartbeat of the present invention, so that a variety of health information may be read out therewith. Furthermore, the algorithm of the present invention analyzes values such as differences between the median of heartbeat intervals and each heartbeat interval, average of the each heartbeat intervals, standard deviation of each heartbeat intervals and difference between consecutive two heartbeat intervals, and performs rapid calculation without complicate calculation or analysis. Moreover, less obvious atrial fibrillation may be detected out by the method of the present invention with its optimization of signal filtration.

Besides high accuracy and rapid calculation for signal filtration, the wearable device with the method of diagnosing personal cardiac health condition by monitoring and analyzing heartbeat may avoid judgment on the user in the motion state by judging user's motion signal in a motion state prior to judging and analyzing user's signal of heartbeat interval, so that erroneous judgment can be reduced, unnecessary power consumption may be saved and the efficiency of detection result may be ensured. Moreover, there is not huge raw data transmission and analysis between the wearable device and exterior electric equipment because a microprocessor in the wearable device of the present invention may perform signal process, thus power consumption on wireless transmission can be reduced and convenience in use can be achieved, as well as compact volume. Accordingly, drawbacks such as little power consumption, small volume, poor precise and accurate analysis on signal on traditional wearable device with health estimation can be reduced and solved by the wearable device with the method of diagnosing personal cardiac health condition by monitoring and analyzing heartbeat according to the present invention. The performance of a wearable device of health detection function can be enhanced by the one of the present invention.

BRIEF DESCRIPTION OF THE DRAWINGS

The present invention will be apparent to those skilled in the art by reading the following description of a preferred embodiment thereof with reference to the drawings, in which.

DETAILED DESCRIPTION OF THE PREFERRED EMBODIMENT

The present invention involves a wearable device which diagnoses personal cardiac health condition by monitoring and analyzing heartbeat. User's heartbeat signal may be measured with one or more sensors on the wearable device and utilized to judge personal health. The basic principles and functions of a wearable device will not be illustrated herein because they are well known by one of skilled in the art. However, some characteristics of a wearable device related to the present invention will be illustrated in detailed in the following paragraphs. Besides, in present invention, heartbeat related data such as "heart rhythm" or "heart rate" are used to further distinguish the cardiovascular health condition of user. It is well known by one of skilled in the art that "heart rate" and "heart rhythm" are both heartbeat related data gained by heart beat that can demonstrate the health condition of heart, and the value of "heart rate" can be calculated by both raw heartbeat data and "heart rhythm". Furthermore, the figures of the present invention will not be drawn with real sizes or ratios and only described schematically.

Figure 1:
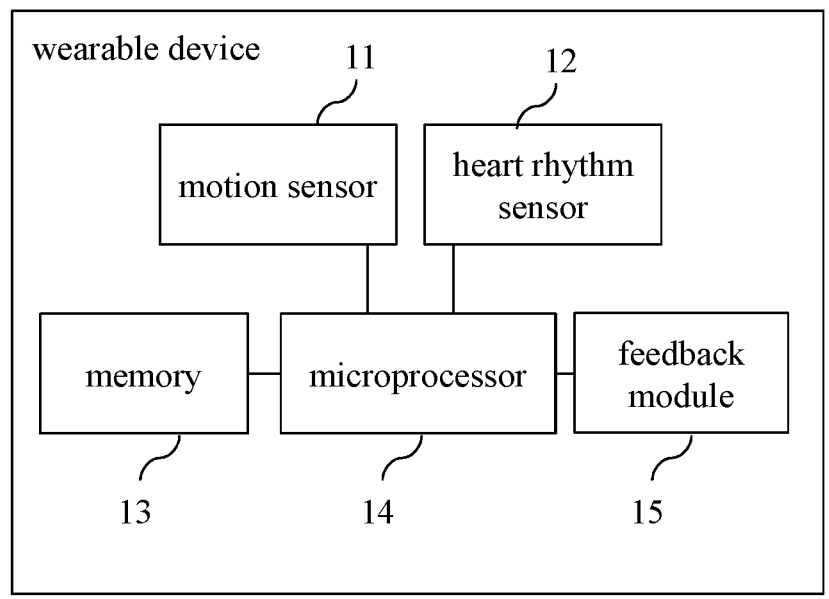
FIG. 1 is a schematic system diagram illustrating a wearable device according to the present invention.

FIG. 1 is a schematic system diagram illustrating a wearable device according to the present invention. Please refer to FIG. 1, a wearable device 1 includes a motion sensor 11, a heart rhythm sensor 12, a memory 13, a microprocessor 14, and a feedback module 15. The motion sensor 11, the heart rhythm sensor 12, the memory 13, and the feedback module 15 are electrically coupled with the microprocessor 14, respectively. The motion sensor 11 may detect user's motion signals and transmit the motion signals to the microprocessor 14. In an embodiment, the motion sensor 11 may be an acceleration sensor, such as a linear acceleration sensor (gravity sensor, G sensor). The heart rhythm sensor 12 may detect user's signals associated with heart beats and transmit these detected signals associated with heart beats to the microprocessor 14. In an embodiment, the heart rhythm sensor 12 measures heartbeat signals by using transmittance measurement method (PhotoPlethysmoGraphy, PPG) to detect alternate heartbeat interval signals as the detected signals associated with heart beats aforementioned, such as high-resolution heartbeat interval (RR interval). However, it is not limited to use the transmittance measurement method in the present invention. The memory 13 may store all necessary information for the operation of the wearable device 1. In an embodiment, the memory 13 may store algorithm programming of cardiac arrhythmia and reference database for signal process and signal filtering or selection. The microprocessor 14 may execute the signal process, signal calculation and signal judgment. For example, after receiving physiological signals from the motion sensor 11 and the heart rhythm sensor 12, the microprocessor 14 may immediately execute following works in a preset period: judging whether motion signals transmitted back from the motion sensor 11 are smaller than a preset motion signal threshold, calculating heartbeat counts in a preset interval and heartbeat intervals corresponding to the heartbeat count, calculating median of the heartbeat intervals, mean of the heartbeat intervals, standard deviation of the heartbeat intervals, or time differences from consecutive heart beats, comparing the time differences among the heartbeat intervals and the median of the heartbeat intervals to acquire difference between them for finding out positions of irregular pulses and judging when and where these irregular pulses happen. The feedback module 15 may receive the signals of the microprocessor 14 to display or make feedbacks in the aural, visual or tactile way, but it is not limited to in the present invention. In an embodiment, the feedback module 15 is a display, acoustic instrument such as speaker, tactile feedback module such as vibration module, or combination of the display, the acoustic instrument and the tactile feedback module. Provided that the signals calculated, compared, and judged by the microprocessor 14 is atrial fibrillation one, they may be transmitted to the feedback module 15 for feedback.

Figure 2:
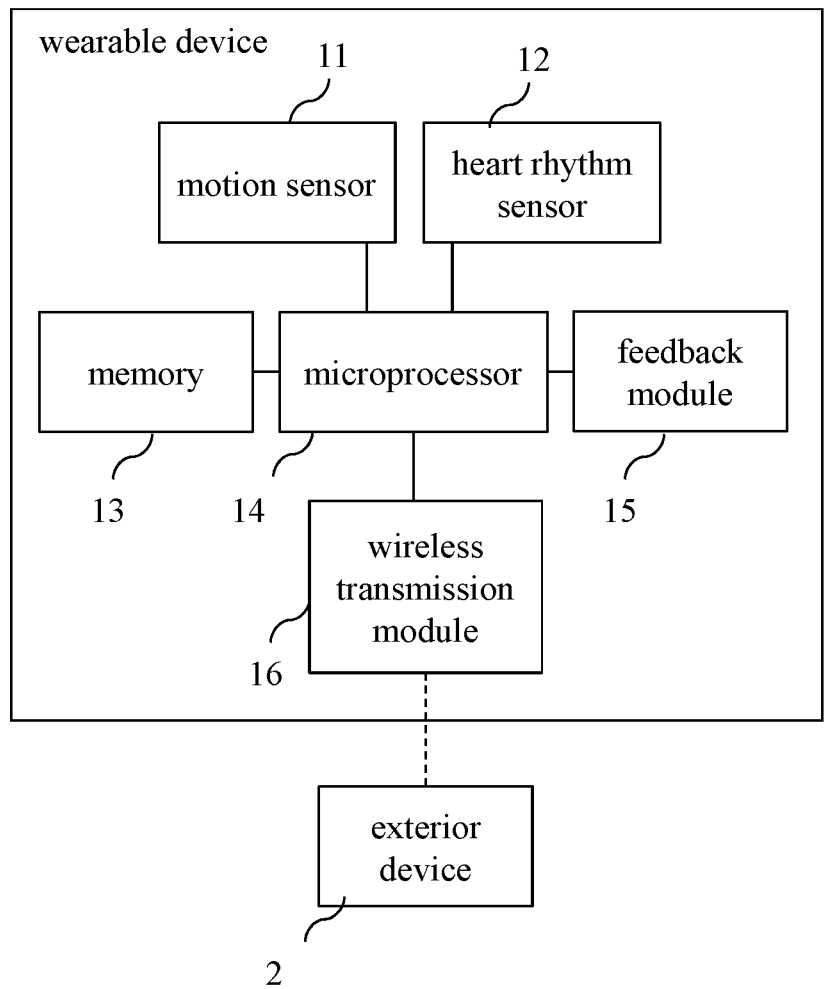
FIG. 2 is a schematic system diagram illustrating another wearable device according to the present invention.

FIG. 2 is a schematic system diagram illustrating another wearable device according to the present invention. Please refer to FIG. 2, the wearable device 1 includes the motion sensor 11, the heart rhythm sensor 12, the memory 13, and the feedback module 15. The motion sensor 11, the heart rhythm sensor 12, the memory 13, and the feedback module 15 are electrically coupled with the microprocessor 14, respectively. The wearable device 1 may further include a wireless transmission module 16. The implement of the motion sensor 11, the heart rhythm sensor 12, the memory 13, and the feedback module 15 are same as the ones of FIG. 1. The wireless transmission module 16 is wirelessly coupled to an exterior device 2 to output information detected and judged by the wearable device 1 or input information or commands from the exterior device 2. Wireless transmission method implemented by the wireless transmission module 16 may be NFC (Near Field Communication), RFID (Radio Frequency Identification), Bluetooth, IrDA (Infrared Data Association), UWB(Ultra-wideband), IEEE, Hiper LAN, and other NFC or medium/long field communication, but it is not limited to in the present invention. The exterior device 2 may be smart phone, tablet, desktop, notebook, or other electric device or other exterior device, but it is not limited to in the present invention.

Figure 3:
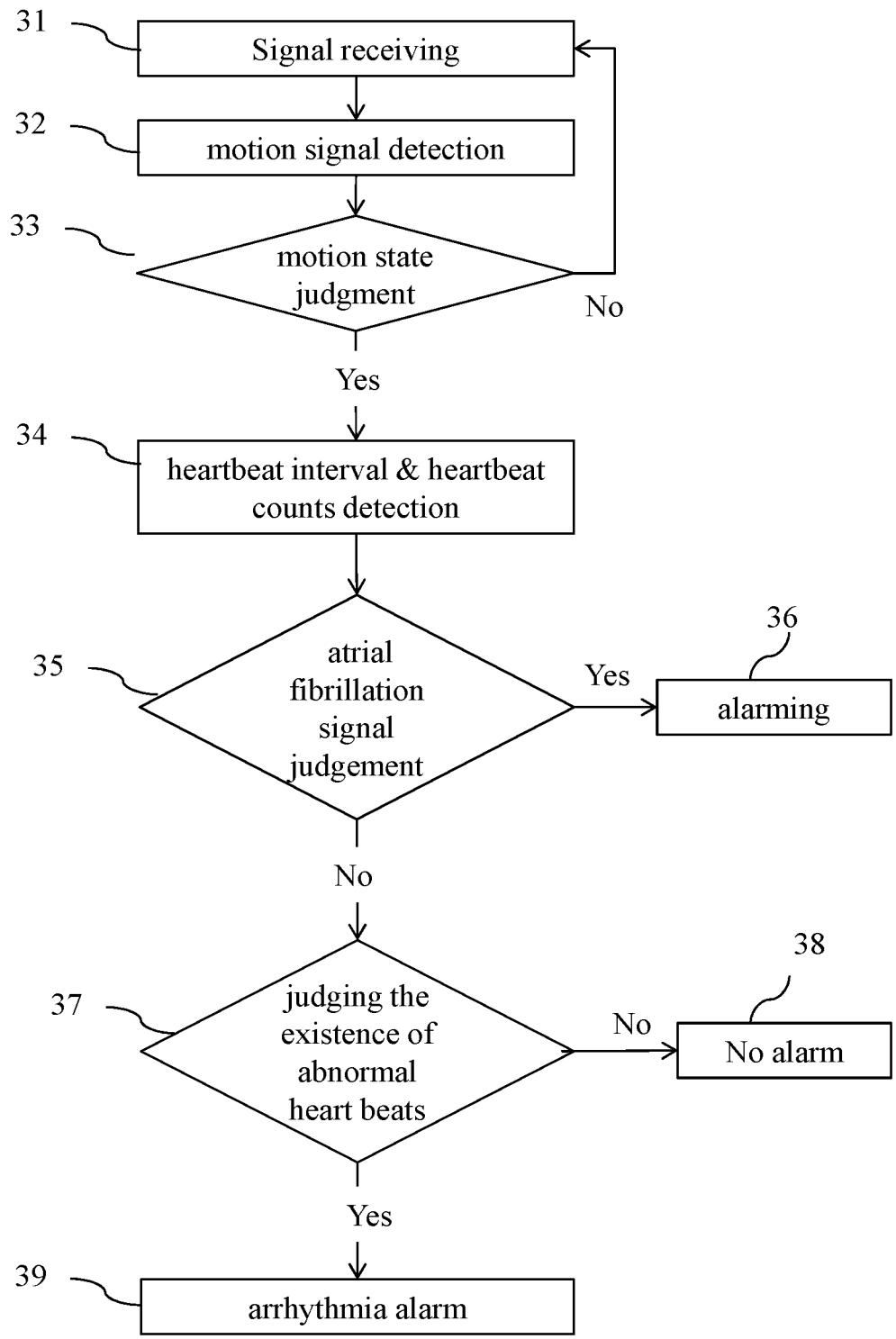
FIG. 3 is a schematic diagram illustrating a flowchart of signal process method of personal health estimation with associated heartbeat signals according to the present invention.

Next, FIG. 3 is a schematic diagram illustrating a flowchart of signal process method of personal health estimation with associated heartbeat signals according to the present invention. Shown in FIG. 3, the signal process method of personal health estimation with associated heartbeat signals includes the steps as follows. Signal is received in step 31. User's motion signal may be consecutively received by the motion sensor 11. Next, the state of the motion signal is detected in step 32. The microprocessor 14 processes the motion signal from the motion sensor 11 and converts it into a value that can be compared with a threshold of motion state. Furthermore, the motion signal may be an average displacement per second sensed by the acceleration sensor. Next, the motion signal is compared with the threshold of motion state in step 33. In step 33, the microprocessor 14 compares the converted value of the motion signal with the threshold of motion state to judge whether the user is in a motion state. That the value converted from the user's motion state is more that the threshold of motion state means the user is in the motion state, and the procedure will go back step 31 for consecutively receiving signals. Provided that the value converted from the user's motion state is fewer that the threshold of motion state, the user will be judged not to be in the motion state, and then the procedure will go the next step for detection of heartbeat signal. In step 33, the threshold of motion state may be set to 0.1~2G of the average displacement per second, but it is not limited to in the present invention. It is noted that from step 31 to step 33 are regular detection steps, and the wearable device 1 of the present invention will execute these regular detection steps. Detection of heartbeat signal starts on condition that the user is judged not to be in the motion state. Optionally, in addition to steps 31-33 of the regular detection steps, the user may manually start the detection of motion signal with a control panel (not shown in the drawings) equipped for the wearable device 1, if he or she feels not well. If the detection of motion signal is manually started by the user, the detection step for the detection of motion signal will regard the user as being in the motion state, and the detection of heartbeat signal will not be executed.

Next, please refer to step 34 of FIG. 3, the heart rhythm sensor 12 detects the signal of heartbeat interval and calculates the heartbeat counts. On condition that the user is judged not to be in a strong exercise state (motion state) in a regular detecting step, the heart rhythm sensor 12 detects the user's signal of heartbeat interval and the heartbeat counts in a preset interval. In the present invention, the preset interval may be an appropriate and fixed time interval, such as 10 seconds to 5 minutes, and it is not limited to in the present invention. Then the heart rhythm sensor 12 transmits the signal of heartbeat interval and the heartbeat counts to the microprocessor 14. Next, whether there is atrial fibrillation signal is judged in step 35. The microprocessor 14 judges whether there is the atrial fibrillation signal according to the signal of heartbeat interval, the heartbeat count, and standard deviation, and so on. If it is judged to be the atrial fibrillation signal, step 36 will be executed to make alarming. If it is not the atrial fibrillation signal, step 37 will be executed to judge whether there is abnormal heart beat. The abnormal heart beat in the present invention includes premature wave, rapid heartbeat, slow heartbeat, and particular form of heartbeat signal. The normal heart beats are signals derived from sinoatrial node. Step 38 will be executed if there is not abnormal heart beats judged, and no alarm will be sent out. If any abnormal heart beat is judged, it will proceed to step 39 to delivery an arrhythmia alarm. It is noted that from step 34 to step 39 are detection steps of heartbeat signal. Accordingly, steps 31-33 of the regular detection steps will go through first to judge whether the user is in exercise or motion state, and then steps 34-39 of the detection steps of heartbeat signal will be executed for detecting and warning atrial fibrillation condition when the user is judged not to be in exercise or motion state. The details of steps 34-39 will be illustrated in following paragraphs.

Figure 4:
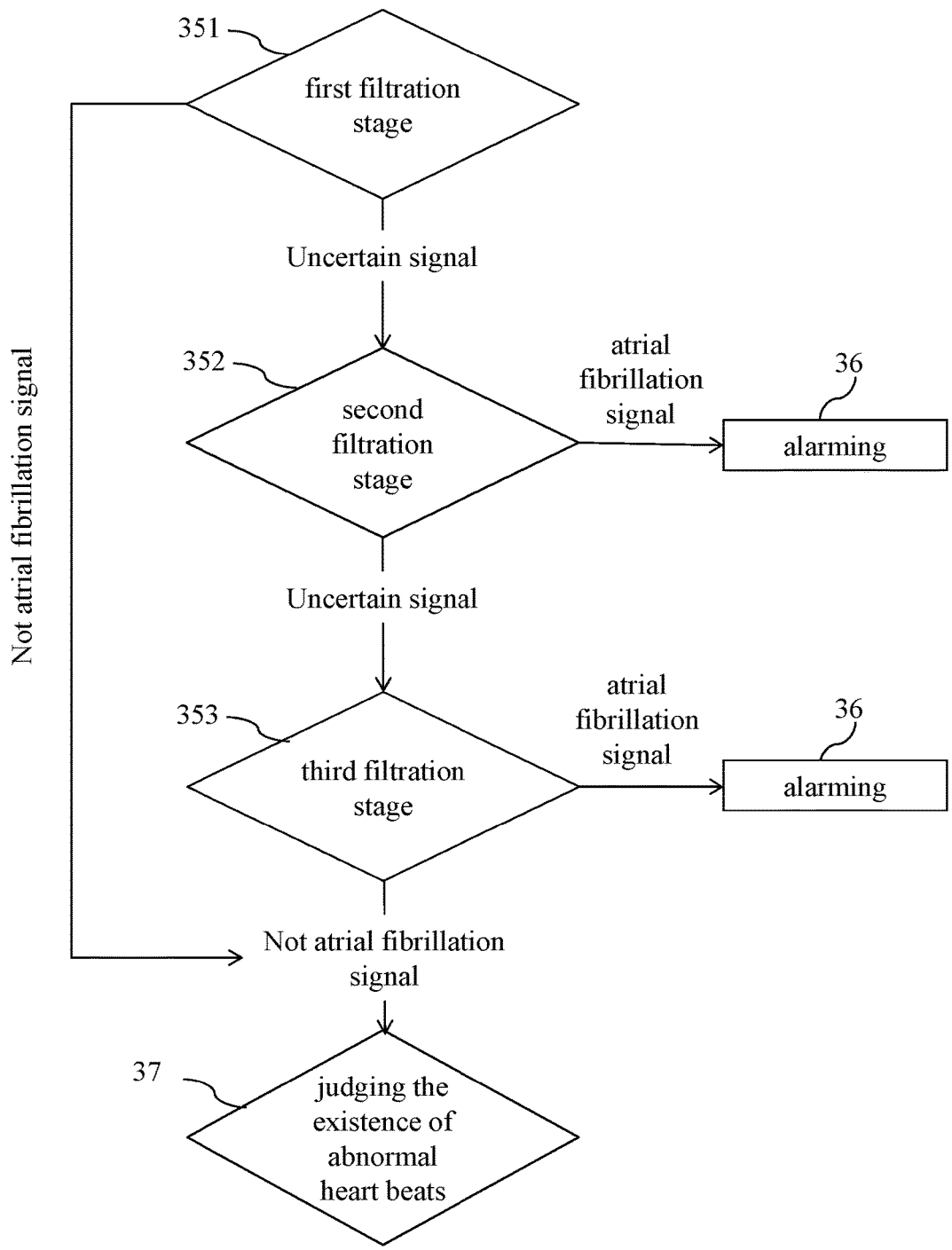
FIG. 4 is a schematic flow diagram illustrating filtration for the detected atrial fibrillation signal according to the present invention.

FIG. 4 is a schematic flow diagram illustrating filtration for the detected atrial fibrillation signal according to the present invention. The detected signal may be judged whether it is atrial fibrillation in step 35. Step 35 includes some signal processing and signal filtration stages. Step 351: that whether the detected signal is non-atrial fibrillation is determined in step 351 of the first filtration stage. If the detected signal is first determined to be non-atrial fibrillation signal in step 351, step 37 for judging existence of the abnormal heartbeats is next executed. If the detected signal is possible atrial fibrillation signal, the process goes into step 352 of the second filtration stage. In step 352, the detected signal that is supposed to be atrial fibrillation in step 351 may be further filtered out to determine whether it is atrial fibrillation and step 36 may be executed for alarming atrial fibrillation. In other embodiments of the present invention, there may be the third filtration stage. After the second filtration stage of screening/excluding out the abnormal heartbeat signal, the process may execute step 353 of the third filtration stage provided that left uncertain signal is over a preset level, such as heartbeat count more than 6 to 10 counts. By passing the third filtration stage, unobvious atrial fibrillation signal may be filtered out and then the process may execute step 36 for alarming the warning of atrial fibrillation. It of course goes into step 37 for judging the existence of abnormal heart beats if it is not atrial fibrillation signal.

Figure 5:
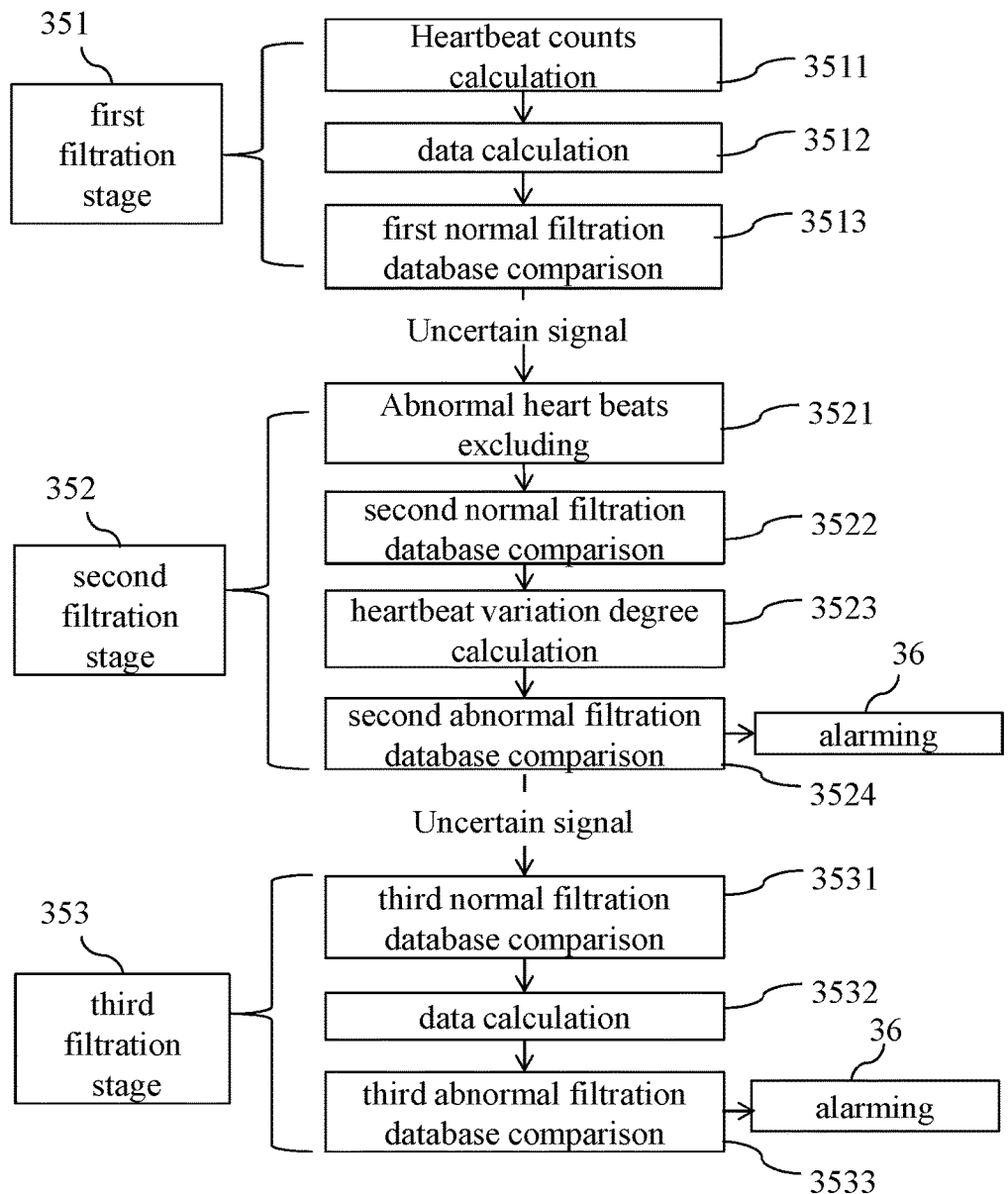
FIG. 5 is a schematic flow diagram illustrating filtration in detail for the detected atrial fibrillation signal according to the present invention.

FIG. 5 is a schematic flow diagram illustrating filtration in detail for the detected atrial fibrillation signal according to the present invention. Shown in FIG. 5, the detection process of atrial fibrillation includes step 351 of the first filtration stage and step 352 of the second filtration stage. In other embodiments of the present invention, the detection process of atrial fibrillation may include step 353 of the third filtration stage. In these filtration stages, the process can go into step 36 for alarming abnormal atrium on condition that the detected signal is determined to be the atrial fibrillation signal. The details of step 351 of the first filtration stages are illustrated as follows. Heartbeat counts are calculated in a preset time period in step 3511 in which the preset time period is appropriated and fixed, such as 5 seconds, 10 minutes, or between 5 seconds and 10 minutes, but it is not limited to in the present invention. Next, average of all heartbeat intervals, standard deviation, and time differences between the consecutive two heartbeat intervals are calculated in the preset time in step 3512. Next, in step 3513, the detected signal is compared with a first normal filtration database to be determined whether it is non-atrial fibrillation. The first normal filtration database may be one or more judgment rules for statistics of healthy heartbeat trend and include average of normal heart rates, standard deviation of heart rates, and distribution and ratio about difference between consecutive two heart rates, and so on. These values from the first normal filtration database can be compared with the ones in step 3512 to filter out signals met with a range of a normal database. In one embodiment, the first normal filtration database includes a numerical in which the average of heart rate is 80-100 bpm and the standard deviation threshold of heart rate is 20. Compared with the numerical of the first normal filtration database, the detected signal that has 80-100 bpm average value of heart rate and the standard deviation of heart rate smaller than 20 is judged to be the non-atrial fibrillation signal. Then the step 37 goes through to judge whether there is abnormal heart beat. In other embodiment, it is not limited to the numerical in the first normal filtration database has the 10-20 standard deviation threshold of heart rate.

Please refer to FIG. 5 again, in step 3513 of the judgment of non-atrial fibrillation signal compared with the numerical of the first normal filtration database, if the detected signal is judged to be abnormal, such as the average value of heart rate not between 80 to 100 bpm and the standard deviation of heart rate more than 20, step 352 of the second filtration stage will be executed. The detailed steps of the second filtration stage are illustrated as follows. Abnormal heart beats will be excluded in step 3521. Those abnormal heart beats are excluded by determining whether the difference between the consecutive two heartbeat intervals and median is more than the threshold of abnormal heart beat. However, the left heartbeat signal is still uncertain. The uncertain heartbeat signal is processed as follows. The time interval difference between the consecutive two heart beats is calculated first and then judged whether it is larger than the threshold of abnormal heart beat. In one embodiment, the threshold of abnormal heart beat may be 5-15 bpm, but it is not limited to in the present invention. That heartbeat difference between the consecutive two heart beats is larger than the threshold of abnormal heart beat is judged to be the abnormal heart beat and excluded. Next, step 3522 of comparison with the second normal filtration database judges whether there is atrial fibrillation. In step 3522, the number of left uncertain heart beats after exclusion of the abnormal heart beats are counted and compared with the second normal filtration database. The second normal filtration database means to include threshold of the number of left signals after exclusion of the abnormal heart beats. For example, the number of signals after exclusion of the abnormal heart beats in the second normal filtration database is 6 heart beats. In the embodiments of the present invention, the threshold of the number of left signals after the exclusion of the abnormal heart beats may be 6-10 heartbeat counts, but it is not limited to in the present invention. If the threshold of the number of left signals in the second normal filtration database is set to be 6 heartbeat counts, after step 3521 of exclusion of abnormal heart beats, that the number of the left uncertain signal is less than 6 heartbeat counts is judged to be not atrial fibrillation signal. Oppositely, that the number of the left uncertain signal is more than 6 heartbeat counts will go into step 3523 of detection of heartbeat variation degree. The heartbeat variation degree of the left uncertain signal after the exclusion step of the abnormal heart beats is calculated for subsequent judgment of the left uncertain signal. The calculation approach of the heartbeat variation degree may calculate a ratio of the heart beats having heartbeat differences within the threshold range to the total heart beats. In one embodiment, the threshold range is set to be the heartbeat difference of 10-40 bpm. Next, go to step 3524 of the comparison with the second abnormal filtration database judges whether there is atrial fibrillation. In step 3524, the heartbeat variation degree calculated in step 3523 may be compared with the second abnormal filtration database for judging whether there is atrial fibrillation. The second abnormal filtration database means to include a threshold of the ratio which is the heart beats having the heartbeat differences within the threshold range to the total heart beats. The threshold range of the heartbeat difference is same as the one in step 3523. In one embodiment, the heartbeat difference may be 10-40 bpm and the threshold of the ratio may be 40-60%. That means, that the heart beats with the heartbeat difference of 10-40 bpm has the ratio over 40-60% of the total heart beats are judged to be atrial fibrillation. If atrial fibrillation is read out in step 3524, step 36 will be executed for alarming atrial fibrillation.

Please refer to FIG. 5, in another embodiment, step 353 of the third filtration stage may execute on condition that the judged heartbeat difference is within the threshold range of the heartbeat difference and the ratio of the judged heart beats to the total heart beats is not over the threshold of the ratio of the second abnormal filtration database in step 3524. Less obvious atrial fibrillation signal may be further filtered out in step 353. The detail steps of the third filtration stage are illustrated as follows. That whether there is atrial fibrillation is judged with the third normal filtration database in step 3531. A judgment rule in step 3531 includes utilizing correlation judgment of abnormal heart beat to determine whether consecutive heartbeat intervals of abnormal heart beats have times as much as the ones of normal heart beats. Abnormal signals are supposed to be correlated with normal signals, provided that not only there is multiple relationship between the consecutive heartbeat intervals of abnormal heart beats and the ones of normal heart beats but also the multiple relationship meets with threshold of multiple relationship in statistics. Such the abnormal signals are possible not to be atrial fibrillation ones but needed to be further analyzed. In one embodiment, the threshold of multiple relationships aforementioned may be any values of 1.3 to 2.5 times, but it is not limited to in the present invention. The correlation of abnormal heart beat may reach 50-80% on condition that the threshold of multiple relationships is from 1.3 to 2.5 times. The signal is judged to be atrial fibrillation one if the correlation of abnormal heart beat does not reach 50-80%, and the process will go into step 36 for alarming atrial fibrillation warning. Oppositely, if the multiple relationship between the consecutive heartbeat intervals of abnormal heart beats and the ones of normal heart beats is 1.3 to 2.5 times, it means the correlation of abnormal heart beat reaches 50-80% and the detected signal needs to be analyzed by step 3532 because atrial fibrillation signal is uncertain. Standard deviation of the left heartbeat intervals are calculated in step 3532. That is, the standard deviation of the left heartbeat intervals after the exclusion of the abnormal heart beats in the second filtration stage are calculated for further filtration and judgment. Next, the signal is judged with the third abnormal filtration database to determine whether it is atrial fibrillation in step 3533. Step 3533 may filter less obvious abnormal signals and utilize the third abnormal filtration database of statistics of heartbeat trend for atrial fibrillation individuals. The judgment rules used in the third abnormal filtration database include average of normal heart rates, average of heart rates, standard deviation of heart rates, and distribution and ratio about difference between consecutive two heart rates, and so on. These values from the third abnormal filtration database can be compared with the ones in step 3532 to filter out signals met with atrial fibrillation data. The statistics approach used in the third abnormal filtration database is same as the ones in the first normal filtration database of step 3513 and the second abnormal filtration database of step 3524, but has the smallest numerical range in third abnormal filtration database to more precisely and severely filter out less obvious atrial fibrillation signals. In one embodiment, the third abnormal filtration database includes a numerical that represents standard deviation threshold of normal heart beat. In one embodiment, the standard deviation threshold of normal heart beat is 5-15 bpm, such as 10 bpm. Provided that the standard deviation threshold of normal heart beat is 10 bpm, a value of more than 10 bpm calculated in step 3532 is judged to be atrial fibrillation and then step 36 may be executed for alarming atrial fibrillation warning.

Figure 6:
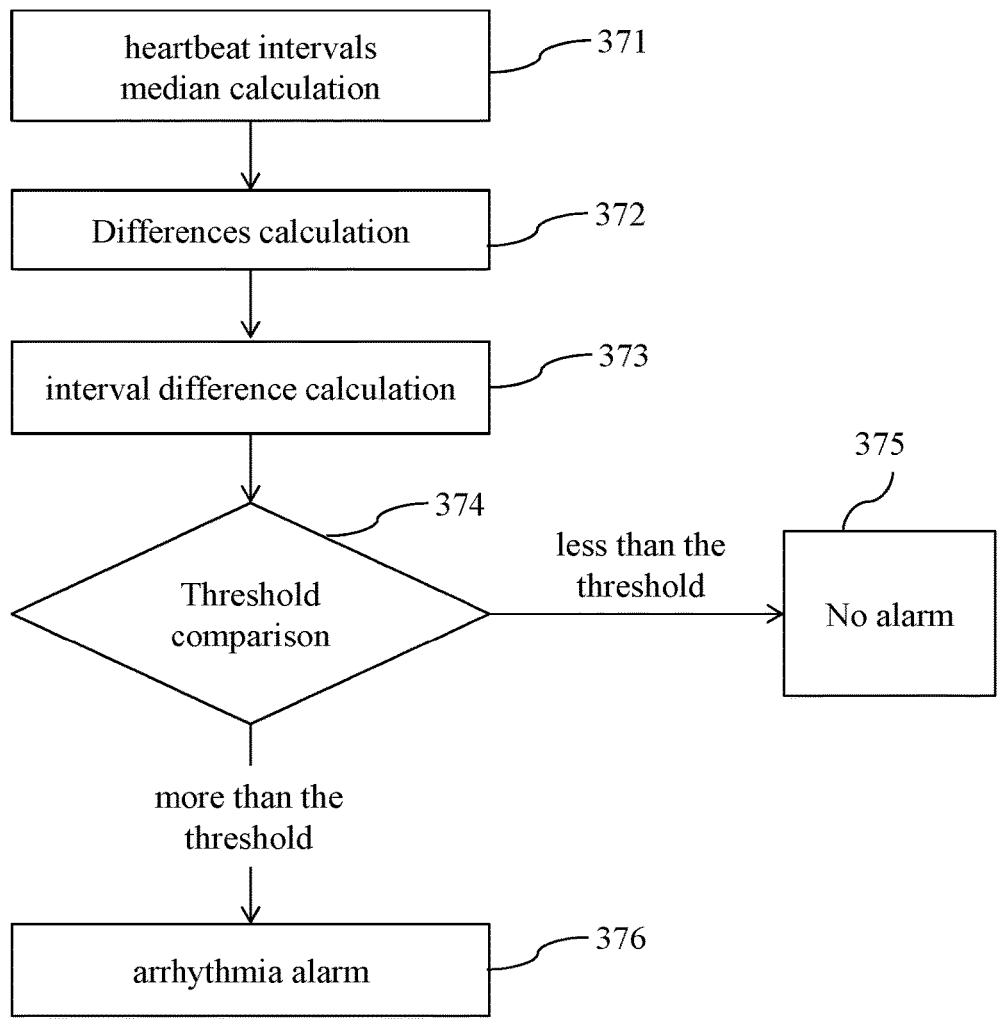
FIG. 6 is a schematic flow diagram illustrating detection of abnormal heart beats according to the present invention.

FIG. 6 is a schematic flow diagram illustrating detection of abnormal heart beats according to the present invention. Shown in FIG. 6, step 37 of judgment of abnormal heart beat includes: median of all heartbeat intervals in a preset time intervals is calculated in step 371. Differences between the median of all heartbeat intervals and the all heartbeat intervals are calculated in step 372. Optionally, interval difference between consecutive heart beats is calculated in step 373 for more precise judgment. Next, that whether difference between the median of all heartbeat intervals and each heartbeat interval is more than the threshold of abnormal heart beat is judged in step 374. In one embodiment, the threshold of abnormal heart beat may be 5-15 bpm, but it is not limited to in the present invention. If the difference between the median of all heartbeat intervals and each heartbeat interval is less than the threshold of abnormal heart beat of 5-15 bpm, there is no abnormal heart beats and step 375 does not execute alarm. Provided that the difference between the median of all heartbeat intervals and each heartbeat interval is more than the threshold of abnormal heart beat of 5-15 bpm, step 376 will be executed to alarm arrhythmia for existence of abnormal heart beat.

In another embodiment, the method of estimating personal health condition by monitoring heartbeat correlated signals further includes step of symptom analysis (not shown in drawings) after the detection step of abnormal heart beat to make precise analysis on heartbeat information. The step of symptom analysis may determine physiological conditions with respect to heart beats, such as arrhythmia, and be executed on the condition of no atrial fibrillation signal. The step of symptom analysis includes: by utilizing rhythm algorithm program, the microprocessor 14 judges positions of abnormal heart beats in the signal of heartbeat intervals. For example, there are 10 waves in whole signal and the second wave is detected to have abnormal heart beat, so the position with respect to the abnormal heart beat is 2. The memory 13 stores information of possible symptoms with respect to each position of abnormal heart beat. The rhythm algorithm program may analyze the detected positions of abnormal heart beats and compare them with data in a database to further determine how the detected position is corresponded to symptom and whether there is premature wave, rapid heartbeat, slow heartbeat, or special rhythm. For example, that there are more than twice intervals between abnormal and normal heart beats will be judged to be double rhythm. Then symptom signal is transmitted to the feedback module 15, such as a display, after the acquisition of analysis result.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A wearable device, comprising:
 a motion sensor that detects whether a user is in a motion state;
 a heart rhythm sensor that detects a heartbeat signal of the user;
 a memory that stores an algorithm program, and further stores a database for data processing, comparison, and analysis;
 a microprocessor that calculates, filters, and judges the heartbeat signal; and
 a feedback module that displays or alarms a judgment result,
 wherein the wearable device continuously detects the user's motion state and heartbeat condition, and detects heart rhythm when the user is not in the motion state to judge whether there is an atrial fibrillation signal, and
 wherein the microprocessor calculates, filters, and judges the heartbeat signal by:
  comparing the heartbeat signal with a first normal filtration database to judge whether there is a non-atrial fibrillation signal;
  excluding abnormal heartbeats from the heartbeat signal to produce an uncertain heartbeat signal;
  counting heartbeats in the uncertain heartbeat signal;
  comparing the uncertain heartbeat signal with a second normal filtration database to judge whether there is the atrial fibrillation signal;
  if a number of heartbeat counts in the uncertain heartbeat signal is greater than a predetermined threshold, calculating a heartbeat variation degree of the uncertain heartbeat signal; and
  comparing the heartbeat variation degree with a second abnormal filtration database to judge whether there is the atrial fibrillation signal.

2. The wearable device of claim 1, further comprising a wireless transmission module.

3. The wearable device of claim 1, wherein the feedback module is a display or an acoustic device.

4. The wearable device of claim 1, wherein the motion sensor is an acceleration sensor.

5. The wearable device of claim 4, wherein the motion sensor is a linear acceleration sensor.

6. The wearable device of claim 1, wherein the heart rhythm sensor detects heartbeat-correlated data by photoplethysmography.

* * * * *